US010934236B2

(12) United States Patent
Hutchings et al.

(10) Patent No.: US 10,934,236 B2
(45) Date of Patent: Mar. 2, 2021

(54) HYDROCARBON OXIDATION (71) Applicant: University College Cardiff Consultants LTD, South Glamorgan (GB)

(72) Inventors: Graham Hutchings, Northallerton (GB); Nishtha Agarwal, Bristol (GB); Simon Freakley, Bristol (GB); Stuart Taylor, South Glamorgan (GB)

(73) Assignee: University College Cardiff Consultants LTD, South Glamorgan (GB)

(*) Notice: Subject to any disclaimer, the term of this patent is extended or adjusted under 35 U.S.C. 154(b) by 0 days.

(21) Appl. No.: 16/612,729

(22) PCT Filed: May 11, 2018

(86) PCT No.: PCT/GB2018/051284
§ 371 (c)(1),
(2) Date: Nov. 11, 2019

(87) PCT Pub. No.: WO2018/206981
PCT Pub. Date: Nov. 15, 2018

(65) Prior Publication Data
US 2020/0079711 A1 Mar. 12, 2020

(30) Foreign Application Priority Data
May 12, 2017 (GB) ..................................... 1707621

(51) Int. Cl.
| C07C 29/48 | (2006.01) |
| B01J 23/52 | (2006.01) |
| B01J 35/00 | (2006.01) |
| B01J 35/02 | (2006.01) |
| B01J 37/16 | (2006.01) |

(52) U.S. Cl.
CPC ............... *C07C 29/48* (2013.01); *B01J 23/52* (2013.01); *B01J 35/006* (2013.01); *B01J 35/008* (2013.01); *B01J 35/0013* (2013.01); *B01J 35/023* (2013.01); *B01J 37/16* (2013.01)

(58) Field of Classification Search
CPC ..... C07C 27/16; C07C 407/00; C07C 51/285; C07C 31/04; C07C 409/04; C07C 53/02; C07C 2523/44; C07C 2523/52; C07C 29/48; B01J 23/52; B01J 35/0013; B01J 35/002; B01J 35/006; B01J 35/008; B01J 35/023; B01J 37/16; Y02P 20/52
See application file for complete search history.

(56) References Cited

U.S. PATENT DOCUMENTS 2,751,417 A 6/1956 Enos, Jr.

FOREIGN PATENT DOCUMENTS

| WO | WO2011/051642 | * | 5/2011 |
| WO | WO 2011/051642 A1 | | 5/2011 |
| WO | WO 2011/051643 A1 | | 5/2011 |

OTHER PUBLICATIONS

White et al (Basic Energy Sciences Advisory Committee Subpanel Workshop Report, Opportunities for Catalysis in the 21st Century, 2002, pp. 1-47) (Year: 2002).*
Zeng et al. (Gold nanoparticles stabilized by task-specific ionic complexes: Quasi-homogeneous catalysts with self-separating nature for aerobic epoxidation of styrene, Journal of Catalysis 319, pp. 163-173, Published 2014) (Year: 2014).*
Boualleg et al. (Highly efficient aerobic oxidation of alkenes over unsupported nanogoldt, Chem. Commun., 46, pp. 5361-5363, Published 2010) (Year: 2010).*
Dimitratos et al. (Catalysis using colloidal-supported gold-based nanoparticles Appl Petrochem Res 4, pp. 85-94, Published 2014) (Year: 2014).*
International Search Report and Written Opinion of the International Searching Authority of PCT/GB2018/051284 dated Aug. 13, 2018; 10 pages.
Malika Boualleg et al., "Highly efficient aerobic oxidation of alkenes over unsupported nanogold", Chemical Communications, vol. 46, No. 29, Jan. 1, 2010, pp. 5361-5363.
Nishtha Agarwal et al., "Aqueous Au—Pd colloids catalyze selective $CH_4$ oxidation to $CH_3OH$ with $O_2$ under mild conditions", Science, vol. 359, No. 6360, Oct. 13, 2017, pp. 223-227; DOI: 10.1126/science.aan6515.
Zeng Aifeng et al. "Gold nanoparticles stabilized by task-specific ionic complexes: Quasi-homogeneous catalysts with self-separating nature for aerobic epoxidation of styrene", Journal of Catalysis, Academic Press, Duluth, MN, US, vol. 319, Sep. 23, 2014, pp. 163-173; doi.org/10.1016/j.jcat.2014.08.012.
Boualleg et al., "Highly efficient aerobic oxidation of alkenes over unsupported nanogold", Chem. Commun., 2010, vol. 46, pp. 5361-5363.
Prati et al., "Gold Colloids: From Quasi-Homogeneous to Heterogeneous Catalytic Systems", Accounts of Chemical Research, 2014, vol. 47, No. 3, pp. 855-863.
Zhang et al., "Crown jewel-structured Au/Pd nanoclusters as novel catalysts for aerobic glucose oxidation", Journal of Nanoscience and Nanotechnology, 2013, vol. 13, pp. 5405-5412.
Zhang et al., "Stable Dispersions of PVP-Protected Au/Pt/Ag Trimetallic Nanoparticles as Highly Active Colloidal Catalysts for Aerobic Glucose Oxidation", The Journal of Physical Chemistry C, 2011, vol. 115, pp. 14883-14891.
Zhang et al.,"Synthesis of Au/Pt bimetallic nanoparticles with a Pt-rich shell and their high catalytic activities for aerobic glucose oxidation", Journal of Colloid and Interface Science, 2013, vol. 394, pp. 166-176.

* cited by examiner

Primary Examiner — Yevgeny Valenrod
Assistant Examiner — Blaine G Doletski
(74) Attorney, Agent, or Firm — Squire Patton Boggs (US) LLP (57) ABSTRACT

A method of direct oxidation of a hydrocarbon to produce an oxygenated reaction product, wherein said method comprises contacting a peroxide and oxygen and the hydrocarbon with a suspension of catalyst particles dispersed in a liquid reaction medium, wherein the catalyst particles are unsupported and comprise at least one transition metal.

12 Claims, 4 Drawing Sheets

HYDROCARBON OXIDATION

This application is a National Stage entry under 35 USC § 371 of PCT/GB2018/051284, filed May 11, 2018, which claims priority to, and the benefit of, GB1707621.7, which was filed May 12, 2017, the entire contents of which are herein incorporated by reference in its entirety for all purposes.

BACKGROUND

The oxidation of hydrocarbons into useful oxygenates has long been an attractive and challenging research area. In particular, it is desirable to be able to transform natural gas, which is inexpensive and in high abundance, into useful products. Natural gas comprises lower alkanes as its main constituents, and can be converted via oxidation to provide products such as alcohols through the use of a heterogeneous catalyst. For example, the industrial utilization of methane currently involves the indirect conversion to methanol via the intermediate production of synthesis gas ($CO+H_2$). The high temperatures and pressures required by this process make it both expensive and energy intensive. In addition, the resulting oxygenated products may lack stability under such harsh conditions, and unwanted carbon oxides such as CO and $CO_2$ may be observed.

Thus, oxidation of hydrocarbons by a direct method may be advantageous. The formation of oxygenated products under milder conditions may also desirable, for example, to reduce or avoid the formation of CO or $CO_2$ and to maintain the stability of the oxygenated products.

WO 2011/051642 describes a process for producing alcohols, such as methanol, that involves contacting hydrogen peroxide and methane in the presence of a heterogeneous catalyst comprising gold on a solid support.

DESCRIPTION OF THE FIGURES

Embodiments of the invention are further described below, by way of example, with reference to the accompanying drawings, in which.

DETAILED DESCRIPTION

Before the present disclosure is disclosed and described, it is to be understood that this disclosure is not limited to the particular process steps and materials disclosed in this disclosure because such process steps and materials may vary. It is also to be understood that the terminology used in this disclosure is used for the purpose of describing particular examples. The terms are not intended to be limiting because the scope is intended to be limited by the appended claims and equivalents thereof.

It is noted that, as used in this specification and the appended claims, the singular forms "a," "an," and "the" include plural referents unless the context clearly dictates otherwise.

According to an aspect of the present invention, there is provided a method of direct oxidation of a hydrocarbon to produce an oxygenated reaction product, wherein said method comprises contacting a peroxide and oxygen and the hydrocarbon with a suspension of catalyst particles dispersed in a liquid reaction medium, wherein the catalyst particles are unsupported and comprise at least one transition metal.

It has been found that, by using a suspension of unsupported catalyst particles in a liquid reaction medium, it may be possible to improve the selectivity of the direct oxidation reaction towards primary oxygenates, for example, alcohols, aldehydes and/or ketones. In other words, by using a suspension of unsupported catalyst particles in a liquid reaction medium, it may be possible to improve the selectivity of the direct oxidation reaction to reduce the formation of, for example, carbon monoxide and/or carbon dioxide.

In particular, it has been found that a suspension of unsupported nanoparticles in a colloidal solution can act as an active and stable catalyst for the selective oxidation of a hydrocarbon (such as methane) to an oxygenated reaction product (such as methanol), by the incorporation of molecular oxygen. The reaction proceeds when an oxidant such as a peroxide is present. The peroxide can be an organic peroxide, such as a peroxy acid or an organic hydroperoxide, or an inorganic peroxide, for example, hydrogen peroxide. The organic peroxide may be of the formula ROOR', wherein each of R and R' is independently selected from hydrogen or a $C_1$-$C_8$ alkyl group, preferably $C_1$-$C_4$ alkyl. In a preferred embodiment, the peroxide is hydrogen peroxide. In another embodiment, the peroxide is tert-butyl hydroperoxide (TBHP). Alternatively, a radical initiator such as azobisisobutyronitrile (AIBN) may be present. Without wishing to be bound by any theory, it is believed that the reaction proceeds via the initial activation of methane, for example, to form methyl radicals. The reaction may proceed through a radical mechanism, such as that shown in Scheme 1 below. In the presence of an unsupported catalyst, radicals such as methyl radicals can react quickly with dissolved $O_2$, resulting in the incorporation of molecular oxygen. More than 70% of the molecular oxygen may be incorporated into the primary reaction products. It is believed that the mechanism shown in Scheme 1 may be suppressed by the presence of a catalyst support.

Scheme 1

Hydrocarbon

The method of the present disclosure may be used in the direct oxidation of any suitable hydrocarbon. The hydrocarbon can be saturated or unsaturated, cyclic or linear or any combination thereof. Examples of suitable hydrocarbons include alkanes and cycloalkanes. In one embodiment, the hydrocarbon is a $C_1$-$C_8$ hydrocarbon. For example, the hydrocarbon may be a $C_1$-$C_8$ alkane, preferably a $C_1$-$C_3$ alkane. Suitable alkanes include methane, ethane, propane, or a combination thereof. In another example, the hydrocarbon is cyclohexane. In another example, the hydrocarbon is octane. Any combination of hydrocarbons may be used.

The hydrocarbon may be contacted with the suspension of catalyst particles dispersed in a liquid reaction medium as a gas or a liquid, preferably a gas. The hydrocarbon may be a gaseous hydrocarbon at room temperature.

Oxygenated Reaction Product

The oxygenated reaction product may comprise a primary oxygenate. Suitable primary oxygenates include alcohols, aldehydes, ketones, carboxylic acids and/or an alkyl hydroperoxide. The alkyl hydroperoxide may be of the formula $C_nH_{2n+1}OOH$, where n is an integer from 1 to 8, for example, 1 to 4. In one embodiment, the primary oxygenate comprises at least one, for example, at least two or three of alcohol, aldehyde, ketone and/or alkyl hydroperoxide.

In one embodiment, the total amount of alcohol, aldehyde, ketone and alkyl hydroperoxide in the oxygenated reaction product forms at least 50 mole % of the total amount of the oxygenated reaction product. Preferably, the total amount of alcohol, aldehyde, ketone and alkyl hydroperoxide in the oxygenated reaction product may be at least 60 mole %, more preferably at least 70 mole %, even more preferably at least 80 mole % or 90 mole % of the total amount of oxygenated reaction product. In one embodiment, the total amount of alcohol, aldehyde, ketone and alkyl hydroperoxide in the oxygenated reaction product may be up to 100 mole %, for example, up to 99 mole % of the total amount of oxygenated reaction product.

Preferably, the oxygenated reaction product comprises an alcohol. In an embodiment, the reaction product comprises a $C_1$-$C_8$ alcohol. For example, the oxygenated reaction product may be selected from methanol, ethanol, propanol, or combinations thereof. In a preferred embodiment, the oxygenated reaction product comprises methanol. Alcohol may form at least 10 mole %, for example, at least 15 mole % of the total amount of oxygenated product. In one embodiment, alcohol may form 10 to 90 mole %, for example, 15 to 80 mole % of the total amount of the oxygenated product.

In another embodiment, the oxygenated reaction product comprises an alkyl hydroperoxide. In an embodiment, the reaction product comprises a $C_1$-$C_8$ alkyl hydroperoxide. For example, the oxygenated reaction product may be selected from methyl hydroperoxide, ethyl hydroperoxide, propyl hydroperoxide, or a combination thereof. In a preferred embodiment, the oxygenated product comprises methyl hydroperoxide. Alkyl hydroperoxide may form at least 10 mole %, for example, at least 15% of the total amount of oxygenated product. In one embodiment, alkyl hydroperoxide may form 10 to 90 mole %, for example 15 to 80 mole % of the total amount of oxygenated product.

In another embodiment, the oxygenated reaction product comprises a carboxylic acid. In an embodiment, the reaction product comprises a $C_1$-$C_8$ carboxylic acid. For example, the oxygenated reaction product may be selected from formic acid, acetic acid, propionic acid, or a combination thereof. In a preferred embodiment, the oxygenated product comprises of formic acid. Formic acid may form less than 50 mole %, for example, less than 30 mole %. In one embodiment formic acid may form 0-40 mole %, for example 0-30 mole % of the total amount of oxygenated product.

In another embodiment, the oxygenated reaction product comprises an aldehyde. For example, the oxygenated reaction product may be selected from $C_1$-$C_8$ aldehyde. For example, the oxygenated reaction may be selected from formaldehyde, acetaldehyde, propanaldehyde or a combination thereof. In a preferred embodiment, the oxygenated product may comprise formaldehyde. Aldehyde may form less than 30 mole %, for example 0-20 mole % of the total amount of oxygenated product.

In a further embodiment, the oxygenated reaction product comprises a ketone. For example, the oxygenated reaction product may be selected from $C_3$-$C_8$ ketone. For example, the oxygenated reaction may be selected from 2-propanone, 2-butanone or a combination thereof. Ketone may form less than 30 mole % for example 0-20 mole % of the total amount of oxygenated product.

The oxygenated reaction product may contain less than 60 mole % carbon dioxide and/or carbon monoxide. Preferably, the oxygenated reaction product may contain less than 50 mole %, more preferably less than 40 mole % or 30 mole % carbon dioxide and/or carbon monoxide. In one embodiment, the oxygenated reaction product may contain less than 20 mole % or 10 mole % carbon dioxide and/or carbon monoxide.

Catalyst

In the present method, the catalyst is a suspension of catalyst particles dispersed in a liquid reaction medium. The catalyst particles are unsupported and comprise at least one transition metal.

By "unsupported", it is meant that at least 70 weight % of the transition metal(s), preferably at least 80, 90% or 95 weight % of the transition metal(s) of the catalyst are not supported or deposited on a solid support. Thus, in one embodiment, the transition metal(s) is not supported on a catalyst support, for example, selected from carbon, ceria, iron oxide, copper oxide, silica, titania and alumina. In some embodiments, the catalyst particles comprise less than 10 weight % carbon, ceria, iron oxide, copper oxide, silica, titania and/or alumina. In some embodiments, the catalyst particles comprise less than 5 weight % or are devoid of carbon, ceria, iron oxide, copper oxide, silica, titania and/or alumina.

Without wishing to be limited by any theory, it has been found that, by omitting a catalyst support material and carrying out the reaction with an unsupported suspension of particles, the selectivity of the direct oxidation reaction can be improved. Without wishing to be bound by any theory, it is believed that catalyst supports can, under certain conditions, catalyse undesirable side reactions that decrease the overall selectivity of the process. This may reduce the total amount of useful oxygenated products, for example, primary oxygenates.

The catalyst particles are a suspension of catalyst particles dispersed in a liquid reaction medium. The suspension may be a colloidal suspension. The catalyst particles may have an average particle size of 1 to 10 nm, preferably 2 to 7 nm, more preferably 3 to 5 nm. Particle size may be determined by any suitable method. For example, transmission electron microscopy or aberration-corrected scanning transmission microscopy can be used to determine particle size.

The transition metal(s) may be present in metallic or alloy form. Thus, the catalyst particles may be formed of particles of metal or metal alloy. The catalyst particles may comprise at least 50 to 100 weight % metal, for example, at least 60, 70, 80 or 90 to 100 weight % metal. In a preferred embodiment, the catalyst particles may comprise 80 or 90 to 100 weight % metal present in metallic or alloy form.

The catalyst particles may be formed from particles of the transition metal(s) or an alloy comprising the transition metal(s). The catalyst particles may have a core-shell structure. For example, the particle core may be formed of a first transition metal and the shell may be formed of a second transition metal. In some examples, the particles may comprise a core and a shell or a series of shells.

Any suitable transition metal may be employed. In a preferred embodiment, the transition metal comprises gold. Preferably, a second transition metal may also be present. Thus, the catalyst may comprise a first transition metal and a second transition metal. The second transition metal may be selected from the group comprising palladium, platinum, copper or a mixture thereof. In a preferred embodiment, the catalyst comprises gold and palladium. In one embodiment, the catalyst comprises at least two, for example, three transition metals.

In one embodiment, the catalyst particles may contain gold in an amount of from 20 to 100 percent by weight based on the total weight of the catalyst, preferably in the range of 40-80 percent by weight, more preferably in the range of 50-70 percent by weight.

Where the catalyst comprises gold and a second transition metal, the second transition metal(s) may be present in an amount of from 0 to 80 percent by weight based on the total weight of the catalyst, preferably in the range of 20-60 percent by weight, more preferably in the range of 30-50 percent by weight. The weight ratio of gold to the second transition metal(s) may be 1:4 to 9:1, preferably 2:3 to 5:4, more preferably 1:1 to 3:1. The second transition metal may be palladium.

In a preferred embodiment, the catalyst comprises gold and palladium. Gold may be present in an amount of 20 to 100 weight %, preferably 40 to 70 weight %. Palladium may be present in an amount of 0 to 80 weight %, preferably 20 to 60 weight %. The weight ratio of gold to palladium may be 1:4 to 8:1, preferably 2:3 to 4:5, more preferably 1:1 to 2:1.

The catalyst particles may be dispersed in a liquid medium. The liquid medium may comprise water. In another embodiment, it may comprise organic solvents, for example acetonitrile, toluene or a combination thereof. In another embodiment, the liquid medium may comprise fluorinated solvents like perfluorobenzene, perfluorotoluene and trifluoroacetic acid. In a preferred embodiment, the liquid medium comprises water.

In some examples, the liquid medium may include a stabilizer for stabilising the (e.g. colloidal) dispersion. The stabilizer may be a polymer, for example polyvinylpyrrolidone (PVP), polyvinyl alcohol, polyethylene glycol, polyacrylic acid, polyaminoamide, poly(sodium acrylate), gelatin, starch, dextrin, carboxymethyl cellulose, methyl cellulose, ethyl cellulose, and glutathione. In particular, polyvinylpyrrolidone, polyvinyl alcohol, polyethylene glycol, polyacrylic acid, poly(sodium acrylate), and carboxymethyl cellulose. The stabilizer may be a surfactant, for example, Triton-X Tetrakishydroxypropylphosphonium chloride (THCP), cetyl trimethylammonium bromide (CTAB) and dodecylbenzenesulfonate. The stabilizer may be an ionic polymer. The stabilizer may be a silane. In a preferred embodiment, the stabilizer is polyvinylpyrrolidone (PVP). The stabilizer may enable the colloidal catalyst particles to be stable over a long period of time. For example, agglomeration of the colloidal particles may be prevented. In another example, precipitation may be avoided.

The amount of stabiliser in the liquid medium may be 0 to 10 weight %, preferably 0 to 5 weight %. In one embodiment, the molar ratio of PVP to transition metal is in the range of 1:1 to 2:1. In a particularly preferred embodiment, the molar ratio of PVP to metal is 1.2:1.

In one embodiment, some of the colloidal particles are immobilized on support materials. In a preferred embodiment, less than 30 weight % of the transition metal(s), preferably less than 20%, 10% or 5 weight % of the transition metal(s) of the catalyst are supported or deposited on a solid support. The support may be carbon, ceria, iron oxide, copper oxide, silica, titania and alumina. In a preferred embodiment, titania ($TiO_2$) is used as the support material. $TiO_2$ may be added to the colloidal catalyst and acidified using sulfuric acid to facilitate immobilization.

Catalyst Preparation

The catalyst can be made by sol preparation. For example, metal solutions may be stabilized and reduced to form colloidal dispersions. In a preferred embodiment, aqueous gold solution can be formed of a suitable salt, for example chloroauric acid ($HAuCl_4$). In one embodiment, palladium may be added through the use of palladium chloride ($PdCl_2$). The aqueous solution's temperature, concentration, pH, and other variables can be adjusted depending on the desired characteristics of the final catalyst. The concentration of gold and other metal or metals can be adjusted relative to each other in order to produce a final catalyst with desired concentration and composition. In one embodiment, the dispersion is stabilized by use of a stabilizer. In a preferred embodiment, PVP is used. Catalyst particles can be produced by reduction using a suitable reductant, for example sodium borohydride, trisodium citrate, or hydrogen. In a preferred embodiment, sodium borohydride is used as the reductant.

Reaction Conditions

The direct oxidation reaction may be carried out by contacting a peroxide (e.g. hydrogen peroxide) and the hydrocarbon with the suspension of catalyst particles dispersed in a liquid reaction medium.

In one embodiment, hydrocarbon can be fed, with or without diluent, either as a gas or a liquid, to the reaction medium, preferably, at pressures from 1 atm to 140 atm, more preferably 8 atm to 100 atm, most preferably from 20 atm to 70 atm. In one embodiment, the peroxide can also be added, with or without diluent, to the reaction medium. The mole ratio of peroxide (e.g. hydrogen peroxide) to hydrocarbon may be between 30 to 2000 micromoles of peroxide (e.g. $H_2O_2$) to 10 mL of reaction medium, preferably between 40 to 120 micromoles of peroxide (e.g. $H_2O_2$) to 10 mL of reaction medium. Without wishing to be bound by any theory, it has been found that, when the relative amount of peroxide (e.g. hydrogen peroxide) to hydrocarbon is kept below a threshold, improvements in selectivity can be observed. In one embodiment, the reaction medium is water.

A fraction of hydrocarbon may be dissolved in the solution. This ratio is dependent on the hydrocarbon, solvent, temperature and pressure.

The concentration of catalyst particles in the liquid reaction medium may be 0.001 to 1 weight %, preferably 0.01 to 0.8 weight %, more preferably, 0.02 to 0.4 weight %.

Any suitable source of peroxide (e.g. hydrogen peroxide) may be employed. In one embodiment where hydrogen peroxide is used, pre-formed hydrogen peroxide is employed. In an alternative embodiment, the hydrogen peroxide may be generated in-situ.

When hydrogen peroxide is generated in-situ, hydrogen and oxygen (e.g. as air or molecular oxygen) may be introduced into the liquid reaction medium. These gases may react at the surface of the catalyst particles to generate hydrogen peroxide in situ. When this hydrogen peroxide contacts hydrocarbon at the catalyst surface, direct oxidation of the hydrocarbon can occur.

Any suitable molar ratio of hydrogen to oxygen may be used to facilitate in situ hydrogen peroxide generation. A suitable molar ratio of hydrogen to oxygen may be 1:5 to 5:1, preferably 1:3 to 3:1, most preferably 1:2 to 2:1. A diluent, for example, methane may be mixed with the hydrogen/oxygen mixture to reduce the risk of explosion.

In one embodiment, oxygen may also be contacted with the suspension of catalyst particles. The oxygen may be introduced as molecular oxygen or air. A suitable ratio of hydrocarbon to oxygen may be employed to reduce the risk of explosion. For example, the ratio may be more than 4:1, preferably more than 5:1. In one embodiment, the oxygen is added after the addition of peroxide (e.g. hydrogen peroxide). In another embodiment, the oxygen and peroxide (e.g. hydrogen peroxide) are added simultaneously.

Addition of oxygen may increase the amount of oxygenated compounds formed. The introduction of oxygen may also allow a reduced amount of peroxide (e.g. $H_2O_2$) to be used. Without wishing to be bound by any theory, it is believed that peroxide (e.g. $H_2O_2$) may act as an initiator for the incorporation of molecular oxygen into the hydrocarbon or hydrocarbons in order to produce an oxygenated product such as an alcohol or a carboxylic acid. For example, the amount of peroxide (e.g. $H_2O_2$) may be reduced to such a level that more oxygenated compounds are produced than would be possible based solely on the amount of peroxide (e.g. $H_2O_2$) consumed.

When employed, the ratio of peroxide (e.g. hydrogen peroxide) to oxygen may be 50-1000 μmol peroxide (e.g. $H_2O_2$) (in reaction solution) to 5 bar $O_2$ (in the gas phase), preferably 50-100 μmol peroxide (e.g. $H_2O_2$) to 5 bar $O_2$, more preferably 60-80 μmol peroxide (e.g. $H_2O_2$) to 5 bar $O_2$.

The direct oxidation can be performed at any suitable temperature. Preferably, the reaction is performed at a low temperature. In one embodiment, the temperature of the reaction may be 0-200° C., preferably 0-100° C., more preferably 60° C. or below, for example 50° C. The direct oxidation can be performed at any suitable pressure. Preferably, the pressure is from 1 atm to 140 atm.

A peroxide can act as a source of radicals (such as OH and $O_2H$ radicals) which initially activate the hydrocarbon to form a radical species (for example, a methyl radical). However, alternative methods of making a radical species from the hydrocarbon may be utilized. In particular, an alternative method of making said radical species under mild conditions, for example at a temperature of under 0-200° C., preferably 0-100° C., more preferably 60° C. or below, and/or a pressure of from 1 atm to 140 atm, may be employed. For example, a suitable source of OH radicals may be utilized. For example, it may be possible to couple a colloidal catalyst (e.g. an AuPd colloidal catalyst) with photochemical or electrochemical fuel cell to generate •OH radicals for H abstraction to facilitate methyl radicals rather than using e.g. hydrogen peroxide.

EXAMPLES

Example 1 Preparation of AuPd Colloidal Catalyst

An aqueous solution of metal precursor $HAuCl_4$ (Sigma Aldrich) and an acidic solution of $PdCl_2$ in 0.5M HCl (Sigma Aldrich) were dissolved in 800 mL of de-ionized water. Polyvinyl pyrrolidone (PVP, average molecular weight 1,300,000) was added as a stabilizer to give the required metal-to-PVP ratio (typically 1:1.2). After 2-3 min of stirring, freshly prepared 0.1M $NaBH_4$ (Sigma Aldrich) solution was added such that the molar ratio of $NaBH_4$-to-metal was 5. This produced a dark brown colloid which was left stirring for 30 minutes to ensure all of the metal precursor was reduced to nanoparticles. The colloid was concentrated using a rotary evaporator to give nominal metal loading of 6.6 μmol per 10 ml.

Figure 1:
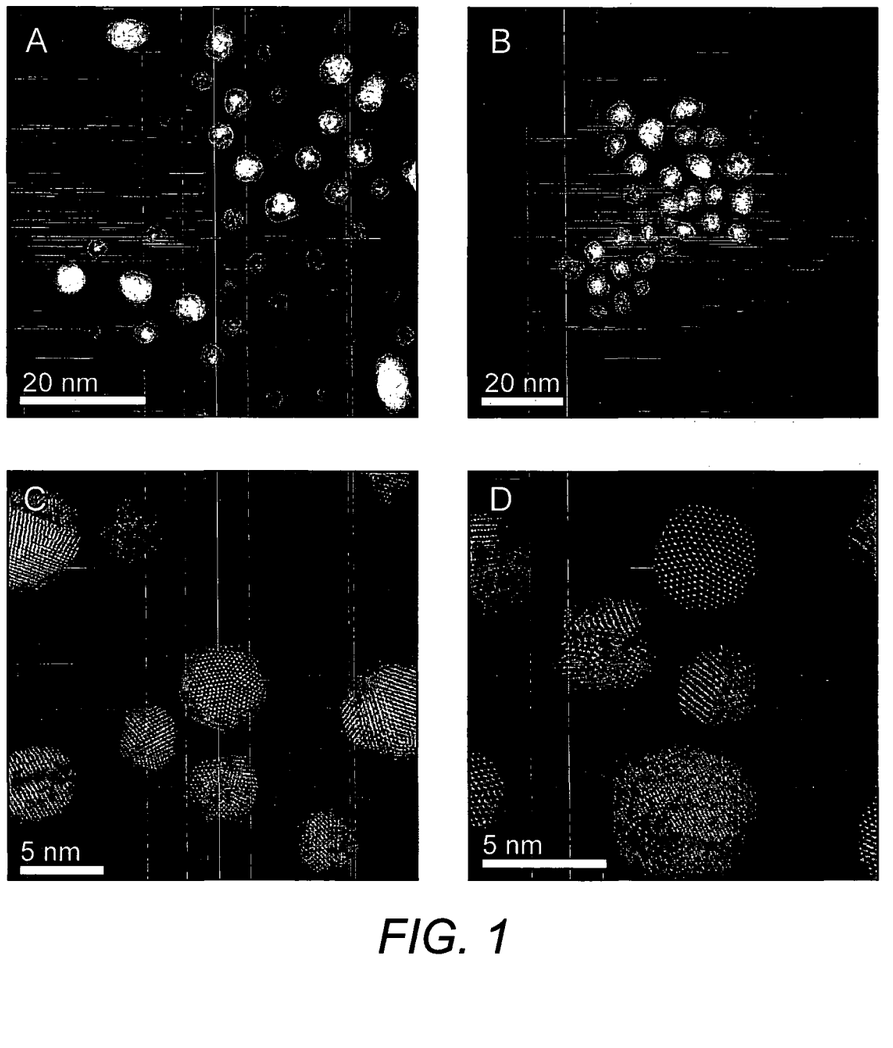
FIG. 1 provides representative HAADF images (A to D) and particle size distributions (E and F) for the unsupported Au—Pd-PVP sol in fresh colloids (A, C, E) and after a $CH_4$ oxidation reaction (B, D, F) in accordance with an embodiment of the invention.

The AuPd colloidal catalyst was characterised by high-angle annular dark field-scanning transmission electron microscopy (HAADF-STEM). FIG. 1 provides representative HAADF images (A and C) and particle size distribution (E) for the unsupported Au—Pd-PVP sol in fresh colloids. HAADF-STEM analysis revealed that the colloids primarily have multiply twinned icosahedral structures, although some cuboctahedral nanoparticles were also detected (A and C). The particle size distribution indicated that the Au—Pd-PVP colloids ranged in size between approx. 2 and 12 nm and had a mean diameter of 3.7 nm (E).

Figure 2:
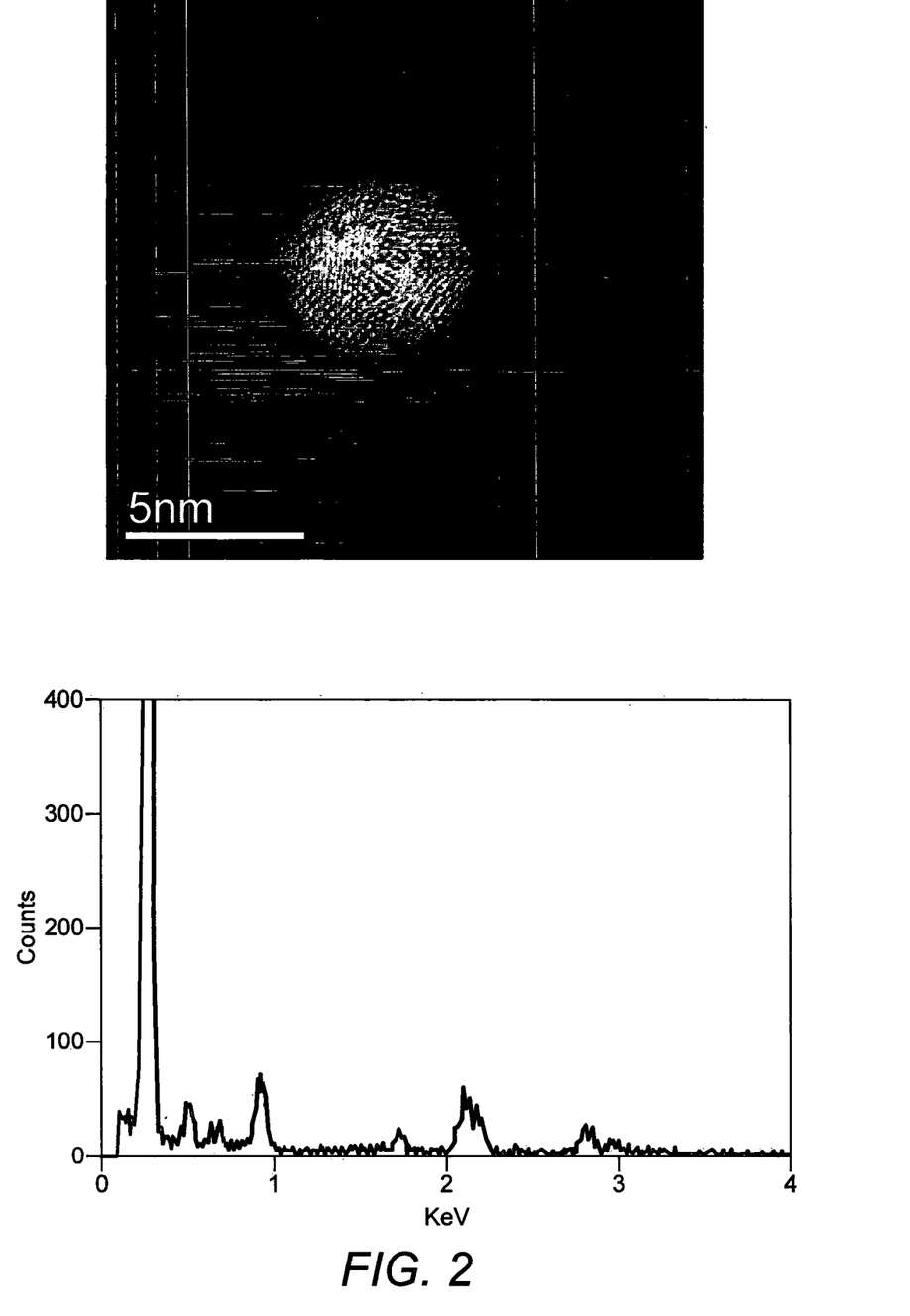
FIG. 2 provides representative XEDS compositional analysis from individual AuPd-PVP nanoparticles from the mid-range of particle size distribution in accordance with an embodiment of the invention.

Further characterisation of the AuPd colloidal catalyst was performed by X-ray energy dispersive spectroscopy (XEDS). FIG. 2 illustrates representative XEDS compositional analysis from individual AuPd-PVP nanoparticles from the mid-range of the particle size distribution. Compositional analysis has shown that the Au—Pd-PVP nanoparticles have a similar Au:Pd ratio, irrespective of their particle size.

Example 2 Liquid Phase Oxidation of Methane with Hydrogen Peroxide and Oxygen Using AuPd Colloidal Catalyst Methane oxidation was carried out in a 50 mL glass lined stainless steel Parr autoclave reactor. The reactor was charged with 10 mL of colloidal catalyst (6.6 μmol metal equivalent) and different amounts of $H_2O_2$ (Sigma Aldrich, 50% wt in water). The charged autoclave was sealed and purged 3 times with methane (99.999%, Air Products). It was then pressurized with methane (30 bar) and oxygen (5 bar, BOC) to remain in oxygen lean limits. It was stirred at 1500 rpm and heated to the desired reaction temperature, (usually 50° C.) and maintained at the reaction temperature for a fixed time (30 min). At the end of reaction, the autoclave was cooled in ice to a temperature below 10° C. to minimize the loss of volatile products, and the reaction gas was removed for analysis in a gas sampling bag. For isotope reactions, BOC specialty gases 98% 18-O enriched $O_2$ gas was used.

Product Analysis

1H-NMR (Bruker 500 MHz) with solvent suppression system was used to quantify liquid phase products with TMS in $CDCl_3$ as internal standard. $H_2O_2$ concentration was determined using a spectrophotometric method (Agilent, Cary 60). 1 mL of reaction sample was acidified using dilute $H_2SO_4$ and then Potassium titanium oxalate solution (0.5% wt in water, Sigma Aldrich) was added to form the yellow pertitanic acid complex with absorption at 390 nm. Gaseous products were quantified using a Varian 450-GC fitted with a CP-Sil 5CB capillary column (50 m length, 0.32 mm diameter carrier gas=He), a methaniser unit and both FID and TCD detectors.

Figure 3:
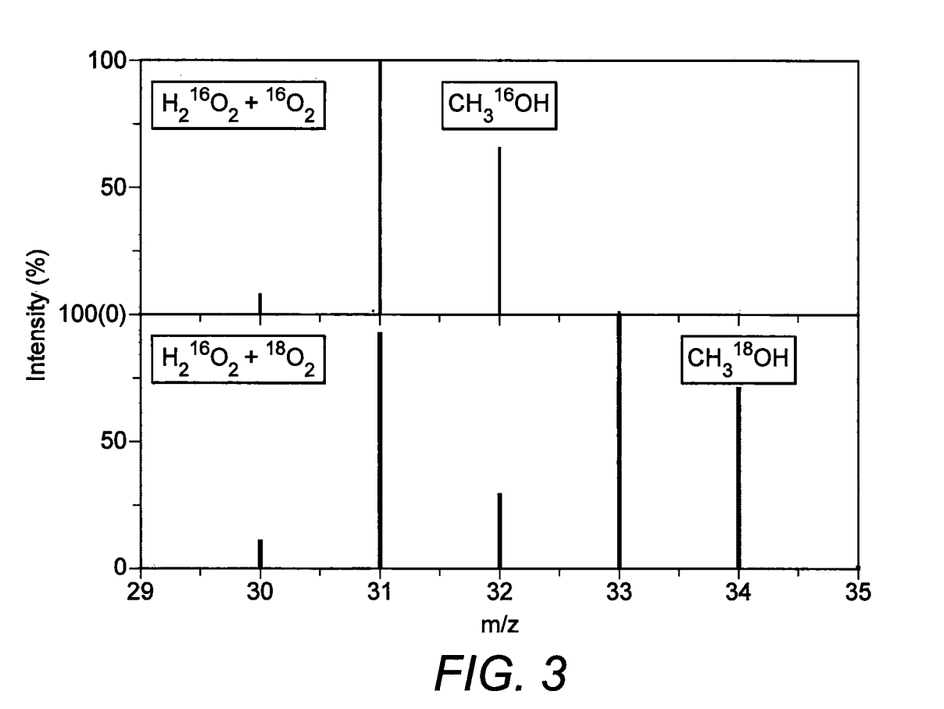
FIG. 3 provides GC-MS spectra of $CH_3OH$ formed (mass=32 and 34 for $CH_3^{16}OH$ and $CH_3^{18}OH$ respectively) during methane oxidation with an Au—Pd colloid via $H_2^{16}O_2+^{16}O_2$ (upper spectrum) or via $H_2^{16}O_2+^{18}O_2$ (lower spectrum) in accordance with an embodiment of the invention.

FIG. 3 shows GC-MS spectra of $CH_3OH$ formed during methane-oxidation. The upper spectrum relates to methane oxidation with an Au—Pd colloid via $H_2^{16}O^2+^{16}O_2$, and the lower spectrum relates to methane oxidation with an Au—Pd colloid via $H_2^{16}O^2+^{18}O_2$. For methane oxidation with $^{18}O_2$, >70% of $^{18}O_2$ molecules were incorporated in the $CH_3OH$ product.

HAADF-STEM analysis of the used colloid revealed some limited particle growth, but no evidence of subnanometer clusters or isolated Au atoms was found either before or after 30 minutes of reaction under optimised conditions, as shown in FIG. 1 (B, D and F).

Table 1 demonstrates the primary oxygenate selectivity, oxygenate productivity and gain factor (gain factor=moles of oxygenate products/moles of hydrogen peroxide used) of liquid phase oxidation of methane with a concentration of $H_2O_2$.

Comparative Example 3 Preparation of 1 Weight % $AuPd/TiO_2$ Catalyst by Sol Immobilization For supported catalysts, sol prepared in example 1 was immobilized on the support material. $TiO_2$ (P25, Degussa, 1.98 g) was added in the aforementioned colloid for 1 weight % metal loading and the solution was acidified to pH 1 using sulphuric acid for better deposition. The supernatant solution becomes clear over 60 min of stirring as the nanoparticles are supported over $TiO_2$. The catalyst is then filtered, washed thoroughly with distilled water and left to dry in an oven at 110 deg for 16 hours.

Comparative Example 4 Liquid Phase Oxidation of Methane with Hydrogen Peroxide and Oxygen Using 1 Weight % $AuPd/TiO_2$ Catalyst The oxidation process in example 2 is repeated with the following modification. In cases with supported catalysts, the reactor was charged with 100 mg of catalyst in 10 mL solution of de-ionized water and $H_2O_2$. And in the end, the reaction mixture was filtered before analysis. As shown in Table 1, minimal reaction products were observed (primary oxygenate selectivity 26%) from oxidation in the presence of the supported catalyst of Example 3. Most of the $H_2O_2$ was decomposed (73% of 1000 μmol consumed). The gain factor, defined as the amount of oxygenated product produced per $H_2O_2$ consumed, was calculated as $2\times10^{-3}$.

In contrast, the colloidal solution produced significantly more products than the supported catalyst, while consuming much less $H_2O_2$, and producing primary products $CH_3OOH$ and $CH_3OH$ at 90% primary oxygenate selectivity. The colloidal catalyst is shown to be an order of magnitude more efficient than the solid $AuPd/TiO_2$ catalyst with respect to products generated per $H_2O_2$ consumed, with a gain factor of $3\times10^{-2}$ compared to $2\times10^{-3}$.

Example 5 Products Generated by Methane Oxidation Using AuPd-PVP Colloid and Varying Amounts of $H_2O_2$ The liquid phase oxidation of methane using a AuPd-PVP colloidal catalyst using different amounts of $H_2O_2$ with $O_2$ was performed. Test conditions: 1.0 h, 50° C. (stirred ramping with ramp rate of 2.25° C./min), 1500 rpm, Cata-

TABLE 1

Comparative catalytic activity of supported and unsupported catalysts for liquid phase oxidation of methane using $H_2O_2$

| Entry | Catalyst | $H_2O_2$ μmol | $O_2$ bar | Product amount (μmol) | | | | Primary Oxygenate Selectivity/ % | Oxygenate Productivity/ mol $kg_{cat}^{-1}$ $h^{-1}$ | $H_2O_2$ Consumed/ % | Gain Factor |
|---|---|---|---|---|---|---|---|---|---|---|---|
| | | | | $CH_3OOH$ | $CH_3OH$ | HCOOH | $CO_2$ | | | | |
| 1 | 1% $AuPd/TiO_2$ | 1000 | — | 0.0 | 0.4 | 0.00 | 1.2 | 26 | 0.03 | 73 | $2\times10^{-3}$ |
| 2 | AuPd Colloid | 1000 | — | 11.8 | 3.3 | 0.6 | 1.1 | 90 | 29.4 | 38 | $3\times10^{-2}$ |
| 3 | AuPd Colloid | 1000 | 5 | 17.4 | 7.6 | 1.8 | 1.5 | 88 | 53.6 | 27 | $9\times10^{-2}$ |
| 4 | AuPd Colloid | — | 5 | 0 | 0 | 0 | 0.2 | — | — | — | — |
| 5 | AuPd Colloid | 50 | 5 | 15.7 | 2.8 | 1.2 | 0.3 | 92 | 39.4 | 44 | 1.2 |
| 6 | Pd Colloid | 50 | 5 | 0 | 0 | 0 | 0.7 | — | — | 22 | — |
| 7 | Au Colloid | 50 | 5 | 0 | 0 | 0 | 0.1 | — | — | 12 | — |
| 8 | $PdCl_2$ | 50 | 5 | 0 | 0 | 0 | 0.3 | — | — | 5 | — |
| 9 | $HAuCl_4$ | 50 | 5 | 0 | 0 | 0 | 0.2 | — | — | 10 | — |

Test conditions: 0.5 h, 1500 rpm, stirred ramping to 50° C., $P(CH_4)$ = 30 bar.
Entry 1: Sol Immobilized solid catalyst, 100 mg (6.6 μmol metal in 10 mL water)
Entry 2-7: Colloidal (0.66 μmol/ml)
Entry 8, 9: Homogeneous metal solution (6.6 μmol metal)

lyst: 10 mL colloidal solution equal 6.6 µmol of metal (1:1 metal molar ratio), Pressure ($CH_4$)=30 bar, Pressure ($O_2$)=5 bar. The results are shown in Table 2.

TABLE 2

Full breakdown of products generated by methane oxidation using AuPd-PVP colloid and varying different amounts of $H_2O_2$.

| Entry | $H_2O_2$ Added (µmol) | Product amount (µmol) | | | | Oxygenate Selectivity/ % [a] | Oxygenate Productivity [b] | $H_2O_2$ Used/ µmol [c] | Gain Factor [d] |
|---|---|---|---|---|---|---|---|---|---|
| | | $CH_3OOH$ | $CH_3OH$ | HCOOH | $CO_2$ | | | | |
| 1 | 2000 | 11.0 | 6.0 | 0.34 | 2.1 | 89.2 | 17.34 | 1622 | 0.01 |
| 2 | 1000 | 27.4 | 12.0 | 3.8 | 2.0 | 95.6 | 43.2 | 638 | 0.07 |
| 3 | 500 | 31.4 | 14.5 | 4.6 | 1.5 | 97.1 | 50.5 | 246 | 0.2 |
| 4 | 100 | 31.1 | 10.3 | 6.4 | 2.2 | 95.6 | 47.8 | 60 | 0.80 |
| 5 | 50 | 18.5 | 5.4 | 2.2 | 1.3 | 95.3 | 26.1 | 22 | 1.2 |
| 6 | 30 | 10.2 | 3.7 | 1.4 | 1.3 | 92.2 | 15.3 | 11 | 1.4 |

[a] Oxygenate selectivity = (mol of oxygenate/total mol of products) * 100
[b] Oxygenates productivity = $mol_{oxygenates}$ $kg_{cat}^{-1}$ $h^{-1}$
[c] Assayed by the titanium oxalate spectrophotometric method
[d] Gain Factor = Moles of oxygenate products/Moles of hydrogen peroxide used Example 6 Liquid Phase Oxidation of Methane Using AuPd-PVP Colloidal Catalyst Using $H_2O_2$ with and without $O_2$, at Different Temperatures The liquid phase oxidation of methane using an AuPd-PVP colloidal catalyst was performed both with $H_2O_2$ and without $H_2O_2$. Test conditions: 0.5 h, Catalyst: 10 mL colloidal AuPd-PVP solution, 6.6 µmol of metal (1:1 metal molar ratio), 1500 rpm, Pressure ($CH_4$)=30 bar. The results are shown in Table 3. In particular, Table 3 shows a higher gain factor in the presence of $H_2O_2$ and oxygen, in comparison to $H_2O_2$ only.

TABLE 3

Liquid phase oxidation of methane using AuPd-PVP colloidal catalyst using $H_2O_2$ with and without $O_2$ at different temperatures.

| Entry | Conditions | Product amount (µmol) | | | | Oxygenate Selectivity/ % [a] | Oxygenate Productivity [b] | $H_2O_2$ Used/ µmol [c] | Gain Factor [d] |
|---|---|---|---|---|---|---|---|---|---|
| | | $CH_3OOH$ | $CH_3OH$ | HCOOH | $CO_2$ | | | | |
| 1 | No Oxygen T: 50° C. | 13.9 | 3.6 | 0.34 | 1.0 | 94 | 35.7 | 41 | 0.44 |
| 2 | No Oxygen T: 23° C. | 4.3 | 0.0 | 0.0 | 0.3 | 93 | 8.6 | 9 | 0.47 |
| 3 | With Oxygen T: 50° C. | 15.7 | 2.8 | 1.2 | 0.3 | 98 | 39.4 | 16 | 1.23 |
| 4 | With Oxygen T: 23° C. | 4.7 | 0.5 | 0.0 | 0.2 | 96 | 10.4 | 4 | 1.35 |

Entry 1: 50° C. (stirred ramping with ramp rate of 2.25° C./min), $H_2O_2$ amount: 50 µmol.
Entry 2: 23° C. (no heating), $H_2O_2$ amount: 50 µmol.
Entry 3: 50° C. (stirred ramping with ramp rate of 2.25° C./min), $H_2O_2$ amount: 50 µmol, Pressure ($O_2$) = 5 bar.
Entry 4: 23° C. (no heating), $H_2O_2$ amount: 50 µmol, P ($O_2$) = 5 bar.
[a] Oxygenate selectivity = (mol of oxygenate/total mol of products) * 100,
[b] Oxygenates productivity = mol oxygenates $kg_{cat}^{-1}$ $h^{-1}$,
[c] Assayed by the titanium oxalate spectrophotometric method
[d] Gain Factor = Moles of oxygenates/Moles of hydrogen peroxide used Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of direct oxidation of a hydrocarbon to produce an oxygenated reaction product, wherein said method comprises contacting a peroxide and oxygen and the hydrocarbon with a suspension of catalyst particles dispersed in a liquid reaction medium, wherein the catalyst particles are unsupported and wherein the catalyst particles comprise at least one transition metal, wherein the catalyst particles comprise an alloy of gold and at least one other transition metal;

and wherein the hydrocarbon is selected from a $C_1$ to $C_8$ alkane.

2. The method of claim 1, wherein the suspension of catalyst particles is a colloidal suspension of catalyst particles.

3. The method of claim 1, wherein the catalyst particles comprise an alloy of gold and palladium.

4. The method of claim 1, wherein the catalyst particles comprise particles having a core comprising a first transition metal and a shell comprising a second transition metal.

5. The method of claim 1, wherein the hydrocarbon is selected from methane, ethane, propane, and a combination thereof.

6. The method of claim 1, wherein said method is performed at a temperature of 80° C. or less.

7. The method of claim 1, wherein said method is performed under a total pressure of 0-140 atm.

8. The method of claim 1, wherein the particles have an average particle diameter of from 1 nm to 10 nm.

9. The method of claim 1, wherein the catalyst comprises 80 to 100 weight % of metal based on the total weight of the catalyst.

10. The method of claim 1, wherein the peroxide is hydrogen peroxide.

11. The method of claim 10, wherein the molar ratio of hydrogen peroxide to hydrocarbon is between 30 to 2000 micromoles of $H_2O_2$ to 10 mL of reaction medium.

12. The method of claim 11, wherein the ratio of hydrogen peroxide to oxygen employed is 50-1000 μmol $H_2O_2$ to 5 bar $O_2$.

* * * * *